United States Patent [19]

Pang

[11] Patent Number: 4,675,282

[45] Date of Patent: Jun. 23, 1987

[54] ASSAY FOR INTERFERON EPSILON

[75] Inventor: Roy H. L. Pang, Medway, Mass.

[73] Assignee: Damon Biotech, Inc., Needham Heights, Mass.

[21] Appl. No.: 628,612

[22] Filed: Jul. 6, 1984

Related U.S. Application Data

[63] Continuation-in-part of Ser. No. 397,610, Jul. 12, 1981, abandoned.

[51] Int. Cl.$^4$ .................. C12Q 1/70; A61K 39/00
[52] U.S. Cl. ............................ 435/5; 435/29; 435/172.3; 435/811; 435/948; 424/85
[58] Field of Search ............ 435/5, 29, 172.3, 811, 435/948; 424/85

[56] References Cited

U.S. PATENT DOCUMENTS 3,910,824 8/1975 Cartwright et al. ............. 435/811

FOREIGN PATENT DOCUMENTS 1443425 7/1976 United Kingdom ............. 435/811

OTHER PUBLICATIONS

Chemical Abstracts, vol. 100, (1984): 21419s.

Primary Examiner—Christine M. Nucker
Assistant Examiner—Stephen C. Wieder

[57] ABSTRACT

Disclosed is an assay procedure for detecting and quantifying interferon epsilon, a new composition of matter having selective antiviral activity on epithelial cells. The assay comprises incubating a preparation believed to contain interferon epsilon with human keratinocyte cells and with human fibroblast cells followed by a virus challenge. The presence of interferon epsilon is indicated if the preparation has antiviral activity on the keratinocytes but no detectable activity on the fibroblasts. The titer of the preparation may be determined by serially diluting it, incubating the dilution with subcultures of keratinocytes, challenging the subcultures with a virus, observing the viability of cells in the cultures, and comparing the results with a standard.

18 Claims, No Drawings

ASSAY FOR INTERFERON EPSILON

This application is a continuation-in-part of Ser. No. 397,610 filed July 12, 1981, abandoned.

BACKGROUND OF THE INVENTION

This invention relates to immunoassay procedures and, in particular, to an assay for the detection of interferon epsilon, an antiviral agent produced by human epithelial cells.

Interferons are materials which have antiviral properties. They are produced by certain types of cells which have been stimulated by exposure to a virus, certain nucleic acids, or antigen/mitogen complexes. Interferons are extremely potent drugs which show great promise as clinical antiviral agents.

Human interferons typically are divided into three types: interferon alpha, produced from human leukocytes or lymphoblastoid cells; interferon beta, produced from fibroblasts; and interferon gamma, produced from human T-lymphocytes. All three are secreted by the respective cells after the cells are stimulated by a virus or an analogous challenge.

U.S. patent application Ser. No. 397,610 now abandoned entitled "Interferon-E" filed July 12, 1981, and a continuation-in-part thereof, Ser. No. 628,327 now U.S. Pat. No. 4,614,651 filed herewith and having the same title, disclose the existence of a fourth type of interferon, called interferon epsilon or interferon E, derived from human epithelial cells. The disclosures of both of these commonly assigned patent applications are hereby incorporated by reference.

Interferon epsilon is active on human epithelial cells and therefore holds promise in augmenting the body's first line of defense, e.g., the skin and other epithelial surfaces, against viral attack. However, because interferon epsilon is active only in the epithelium, conventional tests for interferons are inadequate to detect and quantify its presence. Thus, there exists a need for a simple, effective assay to detect the presence of interferon epsilon and quantify its titer. Such an assay would be useful in laboratory settings as well as in quality control procedures in the manufacture of interferon epsilon for therapeutic use.

SUMMARY OF THE INVENTION

It has been discovered that the presence of interferon epsilon can be quantified readily by observation of its cytopathic effects on epithelial cells, especially keratinocyte cells, treated with samples believed to contain it. Interferon epsilon has antiviral activity on human epithelial cells but no detectable activity on human fibroblasts, and is antigenically distinct from alpha, beta, and gamma interferon. Accordingly, a preparation which exhibits antiviral activity on cells of epithelial origin but no activity on fibroblasts contains interferon epsilon. These observations form the basis for both a quantitative and qualitative assay for interferon epsilon.

The quantitative assay is a challenge assay conducted by steps analogous to those used in the prior art to measure the titer of other interferons, except that epithelial cells, preferably keratinocytes, and most preferably young keratinocytes, are employed in place of fibroblasts. Thus, keratinocytes are grown, divided into plural subcultures, and treated with a sample containing an unknown concentration of interferon epsilon and no contaminating interferons. Each successive cell subculture is treated with a portion of the sample which has undergone, e.g., a two-fold dilution. After an appropriate incubation period (2 hours to about 2 days), the treated keratinocytes are exposed to a virus challenge. In the exemplary embodiment, the challenging virus is a Vesicular Stomititis Virus (VSV).

One unit of interferon epsilon may be defined as the concentration necessary to protect one-half of a human keratinocyte population from challenge with a standard virus concentration. The number of units present in a given uncontaminated sample may accordingly be readily determined.

When interferon epsilon is produced by stimulating epithelial cells with a virus, interferon alpha and interferon beta often also are produced. These will interfere with the foregoing assay. Accordingly, when interferon alpha, beta, or gamma is present, they should be removed or their activity neutralized prior to conducting the assay.

The qualitative assay is conducted by first neutralizing out or otherwise removing any contaminating interferons in the test sample. If the sample then displays antiviral activity on epithelial cells but no detectable activity on human fibroblasts, it contains interferon epsilon.

The assay results must of course be compared to a standard to obtain meaningful data. A standard preparation of interferon epsilon can be made by stimulating epithelial cells, preferably keratinocytes, with a virus, e.g., as disclosed in detail in the Interferon Epsilon application referred to above, harvesting the supernatant after the interferons have been produced and secreted, and then neutralizing the preparation with alpha, beta, and gamma antibodies. The remaining preparation will contain interferon epsilon. This may be serially diluted and added to epithelial cell microcultures until a dilution is reached which will protect one half the epithelial cells in the culture from challenge by of a standard concentration (e.g., one pfu/cell) of a given virus, e.g., vesicular stomatitis virus. This dilution will contain one unit of interferon epsilon activity.

The object of the invention is to provide methods of determining the presence and quantity of interferon epsilon in preparations suspected to contain it.

These and other objects and features of the invention will be apparent from the description and claims which follow.

BRIEF DESCRIPTION OF THE DRAWING

FIG. 1 is a graph showing electrophoresis of the epithelial interferon of the invention.

DESCRIPTION

The above-referenced U.S. patent applications disclose a new type of interferon separate and distinct from the known types of interferon. When the new material, designated interferon epsilon, is produced by stimulating human cells of epithelial origin, other interferons are also produced, and it has been difficult to detect and quantify interferon epsilon in the presence of those other materials.

It has been discovered that interferon epsilon uncontaminated by other known interferons, has high antiviral activity in epithelial cells and no detectable activity on the other types of cells normally employed in interferon challenge assays. Indeed, the definition of a unit of activity conventionally employed for other interferons, i.e., the concentration which protects one-half the cells in a human fibroblast cell culture from challenge with a standard concentration of Vesicular Stomatitis Virus, has no meaning when dealing with interferon epsilon. That is because a concentration of interferon epsilon having significant antiviral activity on epithelial cells has no detectable antiviral activity in fibroblasts.

This marked and selective potency of interferon epsilon in human epithelial cell cultures, and particularly keratinocytes, may be used as a basis to detect and quantify it. One unit of interferon epsilon may be defined as the concentration which protects one-half the cells in a human keratinocyte cell culture from challenge with one pfu/cell of Vesicular Stomatitis Virus.

When it is desired to determine and/or quantify the presence or level of interferon epsilon in a preparation expected to contain other interferons, the activity of the other interferons may be eliminated by neutralization with antibodies to gamma, beta, and alpha interferon, and the preparation may then be tested for its ability to protect human keratinocytes or other human cells of epithelial origin from virus infection. The presence of epsilon interferon is confirmed if a sample purified to remove alpha, beta, and gamma interferon activity is found to have antiviral activity on cells of epithelial origin but no detectable activity on fibroblasts.

The preferred epithelial cells for use in the assay are keratinocytes, and most preferably young keratinocytes, e.g., a culture which has just become confluent. As the cells mature they accumulate keratin, and this apparently complicates the assay by hindering passage of the virus into the cells during challenge.

The preferred viruses used for challenge are those known to be cytotoxic to epithelial cells. VSV works well, but Encephalomyocarditis virus (EMC), Sendai virus, or other viruses may be used. It is preferred to use the same virus to determine a standard concentration as is used in assays compared with the standard. Generally, the sensitivity of the assay will depend on the particular virus selected.

The assay is preferably conducted by first removing the activity of any contaminating interferons which may be present, then serially diluting the sample, and adding the serial dilution to plural keratinocyte cultures. Preferably, a dilution of relatively high concentration or an undiluted aliquot of the test sample is added also to a fibroblast cell culture. The cultures may be contained in conventional microtiter plates, e.g., comprising 96 wells. After incubation the cultures are challenged with the virus. By counting the number of viable cells contained in the wells at a time, for example, when a control well untreated with the sample contains no viable cells, one can determine the IFN-E titer. If the well containing fibroblasts contains nonviable cells but at least some of the keratinocytes have been protected, the presence of INF epsilon is confirmed.

The invention will next be described in connection with certain working examples. However, it should be clear that various changes and modifications can be carried out by those skilled in the art without departing from the spirit or scope of the invention. For example, the assay may be conducted with either purified or unpurified samples. If purified samples of interferon epsilon are to be used, the use of controlled pore glass beads, as described in copending application "Interferon Epsilon", referenced above, can be useful in the purification process.

Additionally, although well plates and visual observation have been described as a preferred apparatus and method for carrying out the assay, it should be clear that various other cell culturing devices and detection methods can be employed. Automated analysis, for example, may be preferred in connection with large scale production of interferon epsilon. Moreover, although young keratinocytes are identified as the preferred cells for assaying interferon epsilon, other epithelial cells can also prove useful. Other viruses may also be used provided they are capable of infecting human epithelial cells.

EXAMPLE 1

An epithelial cell culture of epidermal origin (keratinocytes) obtained from the laboratory of Dr. Howard Green at Massachusetts Institute of Technology was grown to a density of $1-2 \times 10^5$ cells per cm$^2$ and used to produce interferon epsilon employing the Newcastle Disease Virus (NDV) induction method (Baron and Issacs, supra). The virus used was the Bankowski strain of NDV available from Poultry Health Laboratories, Davis, California. Four 1 ml samples of a minimum essential medium (MEM, Gibco) containing 2 percent heat inactivated fetal calf serum ("HIFCS") and NDV to multiplicities of infection ranging from 0 to 250 virus pfu/cell in the test samples were prepared and incubated. The cell cultures were incubated for 24 hours. The medium was then harvested, acidified to pH 2 with 0.1 N HCl, and stored at 4° C. for 5-6 days to inactivate the NDV. This crude interferon preparation was tested for antiviral activity after neutralization of interferon alpha, interferon beta and interferon gamma with antibodies specific for each of the three known interferon types. Neutralization titrations of each interferon were carried out using anti-IFN alpha (NIH), anti-IFN beta (NIH and Y. H. Tan, Calgary University, Calgary, Alberta, Canada), anti-IFN gamma (S. Baron), and mixtures of these antisera. The remaining neutralized preparations were then tested on fibroblast (Human FS-4) and epithelial (Human AR) cultures. The results indicated that interferon epsilon had no detectable antiviral activity on fibroblasts but showed activity against viruses in epithelial cells.

The table below summarizes a complete battery of neutralization and antiviral activity tests:

TABLE I

ANTIVIRAL ACTIVITY OF INTERFERON PREPARATIONS ON HUMAN FS-4 AND AR CELLS

| Sample | Treatment[1] | | | Interferon titer[2] (units/ml) | |
|---|---|---|---|---|---|
| | Anti-α | Anti-β | Anti-γ | Human FS-4 | Human AR |
| IFN-ε | − | − | − | 128 | 64 |
| IFN-ε | + | − | − | 48 | 32 |
| IFN-ε | − | + | − | 24 | 32 |
| IFN-ε | − | − | + | 192 | 32 |
| IFN-ε | + | + | − | <4 | 32 |
| IFN-ε | + | + | + | <4 | 32 |
| IFN-α | − | − | − | 64 | 4 |
| IFN-β | − | − | − | 128 | 16 |
| IFN-α/β | − | − | − | 512 | 16 |
| IFN-γ | − | − | − | 32 | 16 |
| IFN-α/β/γ | − | − | − | 384 | 64 |
| IFN-α/β/γ | + | − | − | 128 | 48 |
| IFN-α/β/γ | − | + | − | 256 | 16 |
| IFN-α/β/γ | − | − | + | N.D. | 16 |
| IFN-α/β/γ | + | + | − | <4 | <4 |
| IFN-α/β/γ | + | + | + | <4 | <4 |

[1]The samples were incubated with excess antiserum, as indicated, at 37° C. for 1 hr. before being assayed for interferon activity.
[2]The interferon titer was determined by a viral cytopathic assay.
[3]N.D. — no data It is apparent from the data that interferon alpha and interferon beta were co-produced with interferon epsilon. Note that neutralization with alpha antibody alone or beta antibody alone reduced the units of interferon activity in both the fibroblast and keratinocyte cultures. Neutralization with both and with a mixture of alpha, beta, and gamma antibodies destroyed all antiviral activity of the preparation on fibroblasts while 32 units/ml activity remained in the keratinocyte cells. This demonstrates the presence of interferon epsilon and confirms that it has selective activity on epithelial cell cultures. This crude preparation contained 32 units of interferon epsilon.

EXAMPLE 2

The effect of culture age of keratinocytes and multiplicity of infection of the inducing virus on the production of epsilon interferon was studied. The interferon epsilon titers were conducted as set forth above. The results are summarized below in Table II:

TABLE II

EFFECT OF CULTURE AGE AND M.O.I. ON IFN-E PRODUCTION

| M.O.I.[1] | Interferon titer[2] (units/$10^6$ cells) | | |
|---|---|---|---|
| | 14 days | 21 days | 27 days |
| 0 | <6 | <3 | <4 |
| 0.1 | 10 | <3 | <4 |
| 1 | 53 | 2 | 8 |
| 2 | 79 | 6 | 16 |
| 5 | 210 | 6 | 16 |
| 10 | 157 | 6 | 16 |
| 20 | 210 | 18 | 32 |
| 50 | 210 | 9 | 32 |
| 70 | ND[3] | 12 | 32 |
| 90 | ND | 9 | 32 |
| 100 | 79 | ND | ND |
| 250 | 79 | ND | ND |

[1] Multiplicity of infection
[2] Interferon samples were incubated with excess interferon alpha and beta antisera before assayed for activity on keratinocytes.
[3] N.D. — No data Table II shows that, at least for keratinocyte-type epithelial cells, younger cells, i.e., almost confluent 14-day old cells, produce more interferon epsilon than do older cells.

EXAMPLE 3

Epithelial interferon materials produced in accordance with Example 1 were partially purified.

The samples were subjected to molecular weight analysis using SDS gel electrophoresis according to the method of Lamelli. The samples were incubated at room temperature for 1 hour in the presence of 1.0 percent SDS, 0.05 M tris-HCl (pH 6.8) buffer, 10 percent (v/v) glycerol, and 0.001 percent bromo phenol blue, loaded onto 12.5 percent polyacrylamide gels, and run for approximately 16 hours. After electrophoresis the lanes containing the molecular weight standards were stained. Interferon containing lanes were sliced into 3 mm slices, and extracted by shaking with 0.5 ml PBS containing 0.5 percent SDS for 20 hours at room temperature. Assays of these fractions were performed employing the conventional challenge assay using fibroblasts and by the assay of the invention after neutralization with alpha, beta, and gamma antibody. The molecular weight of the principal activity peak associated with interferon epsilon was calculated by comparison of its position on the gel with the molecular weight standards.

In FIG. 1, interferon epsilon activity is shown clearly in AR epithelial (keratinocyte) cells. The protein corresponding to the epithelial activity has an apparent molecular weight of about 20,000 and is also dramatically reduced in activity by treatment with beta-mercaptoethanol.

In a separate experiment it was determined that interferon epsilon had no antiviral activity in murine or bovine fibroblast cell cultures.

The invention may be embodies in other specific forms without departing form the spirit and scope thereof. Accordingly, other embodiments are within the following claims.

What is claim is:

1. A method of assaying a sample for the presence of interferon epsilon, the method comprising the step of incubating epithelial cells with a sample containing a unknown quantity of interferon epsilon; exposing the incubated cells to a predetermined quantity of a virus having the ability to infect said cells; and comparing the viability of the exposed cells against a standard unit of interferon epsilon as an indication of the quantity of interferon epsilon present in the sample.

2. The method of claim 1 wherein the epithelial cells are keratinocyte cells.

3. The method of claim 2 wherein the incubation period ranges from about 2 hours to about 2 days.

4. The method of claim 1 wherein the incubated cells are exposed to a vesicular stomatitis virus.

5. The method of claim 1 wherein the step of comparing the viability of the cells against a standard further comprises defining a standard unit of interferon in said assay as that quantity of interferon epsilon necessary to protect one-half the number of the exposed cells from infection by a standard virus concentration.

6. The method of claim 1 comprising the additional step of incubating the sample with fibroblast cells; exposing the incubated fibroblast cells to a virus having the ability to infect said fibroblast cells; and observing the fibroblast cells' viability, whereby the death of said fibroblasts in the presence of said sample coupled with protection of said epithelial cells is indicative of the presence of interferon epsilon.

7. The method of claim 1 wherein the sample contains a contaminating interferon, said method comprising the additional step of neutralizing said sample prior to incubating said cells by exposure to excess type-specific antibody against at least one type of known contaminating interferon.

8. The method of claim 7 wherein the antibody is selected from the group consisting of alpha interferon antibody, beta interferon antibody, gamma interferon antibody and mixtures thereof.

9. The method of claim 8 wherein the antisera is a mixture of alpha and beta interferon antisera.

10. The method of claim 1 comprising the additional step of serially diluting said sample, incubating separate cultures of said epithelial cells with said serially diluted sample, and exposing each of said cultures to said virus.

11. The method of claim 1 wherein said epithelial cells are young keratinocytes cells.

12. A method of detecting the presence of interferon epsilon in a sample, said method comprising the steps of neutralizing a sample containing a unknown quantity of interferon epsilon with antibodies to at least alpha and beta interferon; incubating said neutralized sample with human epithelial cells, exposing the incubated cells to a predetermined quantity of virus having the ability to infect said cells, and comparing the viability of the challenged cells against a standard unit of interferon epsilon as an indication of the quantity of interferon epsilon present in the sample.

13. The method of claim 12 wherein said standard unit of interferon epsilon comprises a purified sample of interferon epsilon at a known concentration.

14. The method of claim 13 wherein said purified sample is prepared by stimulating a human epithelial cell culture to produce interferons, harvesting said interferons, and neutralizing any interferon alpha, beta and gamma produced with antibodies.

15. The method of claim 14 wherein the epithelial cells used to prepare said purified sample comprises young keratinocyte cells.

16. The method of claim 12 wherein said epithelial cells are keratinocytes.

17. The method of claim 12 comprising the additonal steps of incubating the sample with fibroblast cells; exposing the incubated fibroblast cells to a virus having the ability to infect said fibroblast cells; and observing the fibroblast cells' viability, whereby the death of said fibroblasts in the presence of said sample coupled with protection of said epithelial cells is indicative of the presence of interferon epsilon.

18. A method of detecting the presence of interferon epsilon in a sample, said method comprising the steps of neutralizing a sample containing a unknown quantity of interferon epsilon with antibodies to at least alpha and beta interferon; incubating said neutralized sample with young human keratinocyte cells, exposing the incubated cells to a predetermined quantity of virus having the ability to infect said cells, and comparing the viability of the challenged cells against a standard unit of interferon epsilon as an indication of the quantity of interferon epsilon present in the sample.

* * * * *